Figure 1:
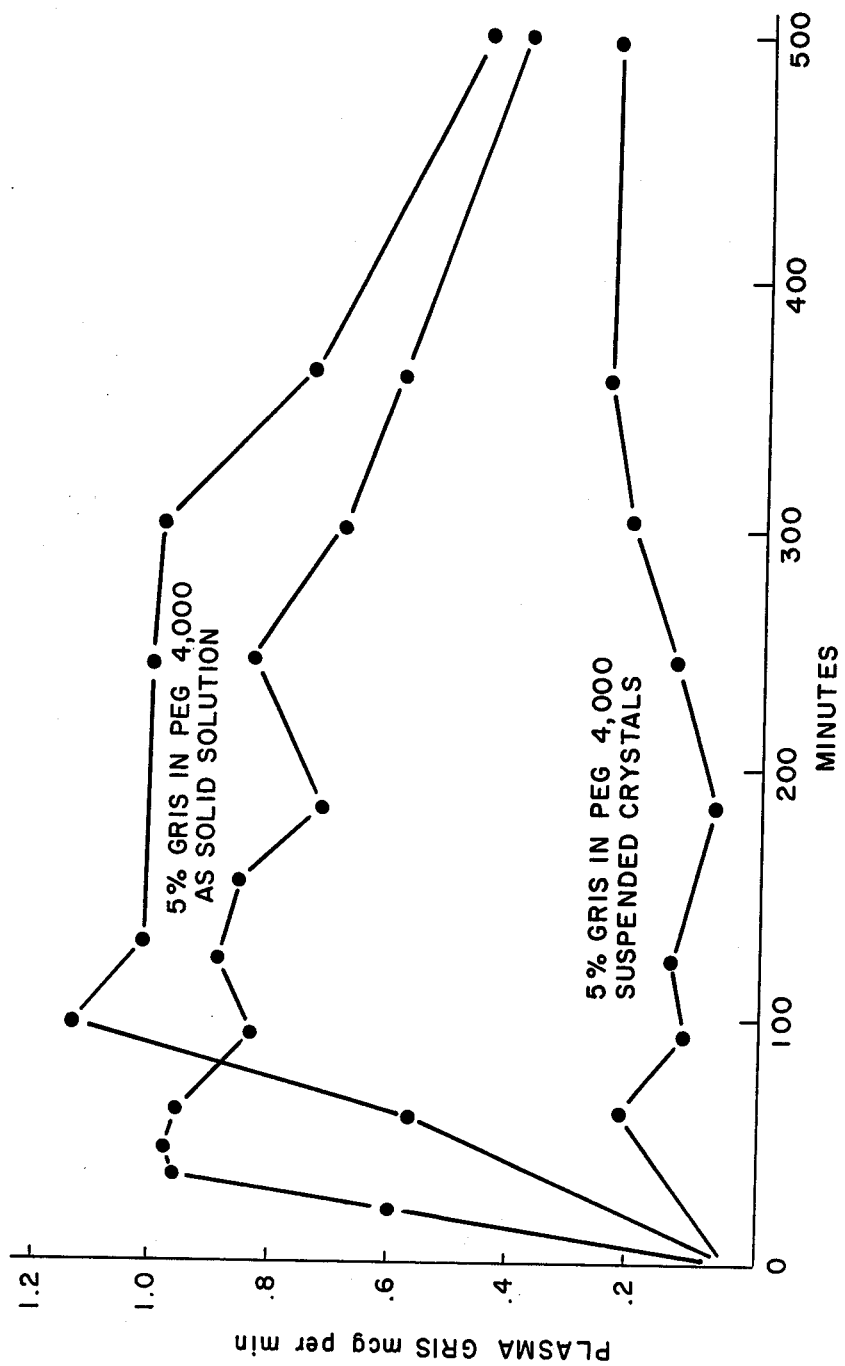

United States Patent [19]

Riegelman et al.

[11] 4,151,273

[45] Apr. 24, 1979

[54] INCREASING THE ABSORPTION RATE OF INSOLUBLE DRUGS

[75] Inventors: Sidney Riegelman, San Francisco, Calif.; Win L. Chiou, Glen Ellyn, Ill.

[73] Assignee: The Regents of the University of California, Berkeley, Calif.

[21] Appl. No.: 915,007

[22] Filed: Jun. 13, 1978

Related U.S. Application Data

[63] Continuation of Ser. No. 519,569, Oct. 31, 1974, abandoned, which is a continuation-in-part of Ser. No. 243,852, Apr. 13, 1972, abandoned, which is a continuation-in-part of Ser. No. 94,499, Dec. 2, 1970, abandoned, which is a continuation-in-part of Ser. No. 10, Jan. 2, 1970, abandoned.

[51] Int. Cl.² .............. A61K 47/00; A61K 31/34; A61K 31/74; A61K 9/20
[52] U.S. Cl. .................................... 424/78; 424/181; 424/182; 424/243; 424/254; 424/260; 424/271; 424/285; 424/298; 424/319
[58] Field of Search ........................... 424/78, 285

[56] References Cited

U.S. PATENT DOCUMENTS

| 2,149,005 | 2/1939 | Bockmuhl et al. | 424/78 |
| 2,698,822 | 1/1955 | Halpern et al. | 424/271 |
| 3,297,804 | 1/1967 | Iwamoto et al. | 264/118 |
| 3,308,217 | 3/1967 | Lowy et al. | 264/117 |
| 3,325,362 | 6/1967 | Poole | 424/285 |
| 3,330,727 | 7/1967 | Lees | 424/285 |
| 3,374,146 | 3/1968 | Blicharz et al. | 424/22 |

FOREIGN PATENT DOCUMENTS 1083985 11/1954 Fed. Rep. of Germany.

OTHER PUBLICATIONS

Sekiguchi et al., Chem. Pharm. Bull. 9:866-872 (1961) Studies on Absorption of Eutectic Mixture.
Sekiguchi et al., Chem. Pharm. Bull. 12:134-144 (1964) Studies on Absorption of Eutectic Mixture.
Goldberg et al., J. Pharm. Sci. 54:1145-1148 (1965) Increasing Dissolution Rates and Gastro-Intestinal Absorption of Drugs via Solid Solutions and Eutectic Mixtures.
Chiou et al., J. Pharm. Sci. 58(12):1505-1509, Dec. 1969, Preparation and Dissolution Characteristics of Several Fast-Release Solid Dispersions of Griseofulvin.

*Primary Examiner*—Shep K. Rose
*Attorney, Agent, or Firm*—Gerald D. Sharkin; Robert S. Honor; Walter F. Jewell

[57] ABSTRACT

The absorption in body fluids of poorly soluble drugs is enhanced by forming a glassy solid matrix of a carrier and the drug. A solution of the drug and the carrier is formed at an elevated temperature either with or without a solvent and chilled rapidly to form a solid mass which can be ground to a powder for oral administration in a tablet or capsule.

12 Claims, 3 Drawing Figures

INCREASING THE ABSORPTION RATE OF INSOLUBLE DRUGS

This is a continuation of application Ser. No. 519,569 filed Oct. 31, 1974, now abandoned, which is a continuation-in-part of application Ser. No. 243,852, filed Apr. 13, 1972, now abandoned which in turn is a continuation-in-part of application Ser. No. 94,499, filed Dec. 2, 1970, now abandoned, which in turn is a continuation-in-part of application Ser. No. 10, filed Jan. 2, 1970, now abandoned.

This invention relates to the absorption of drugs. More particularly, it relates to increasing the absorbability of insoluble or relatively insoluble drugs in aqueous gastric fluids.

The poor solubility of some drugs in aqueous gastric fluids leads to erratic and incomplete absorption in the gastrointestinal tract. It is known that a reduction in particle size, e.g., micronization, will enhance solubility and increase absorption; however, the results have not been completely satisfactory as there is a tendency for the fine sized drug particles to agglomerate, thus decreasing their solubility.

The prior art has also taught the preparation of eutectic mixtures and solid solutions of relatively insoluble drugs with a pharmacologically inert, readily soluble carrier. For example, British Pat. No. 942,743 discloses the preparation of a solid solution of an estrogen and a carrier for use as a pessary. The solid solution is prepared by cooling a molten solution of the estrogen and carrier which is then powdered and incorporated into pessaries. However, the reference only provides estrogen pessary compositions which precipitates the drug without contemplating increasing the absorption thereof in an aqueous medium.

It is, therefore, an object of this invention to provide a composition and method for increasing the absorbability of insoluble or relatively insoluble drugs in aqueous gastric fluids of animals, e.g., higher primates, without the disadvantages of the prior art.

This invention provides for a novel method of increasing the absorption in aqueous gastric fluids of insoluble or relatively insoluble drugs by treating a living body with an insoluble or relatively insoluble drug that has been incorporated in a solid solution, e.g., a glass like solid of a carrier.

This invention provides two methods for preparing the solid solutions of drug and carrier, both methods yield the same product. In accordance with one method, the desired drug and the carrier are heated together until the drug is dissolved in the carrier. In accordance with the second method, a volatile, mutual solvent is employed with heating to prepare a solution of the drug in the carrier. The exact temperature required to bring the mixture of the drug and the carrier or the mixture of the drug, carrier and the solvent into solution will vary. It is dependent on the solubility and the concentration of the drug, the carrier used, and the nature and the amount of the solvent used. The volatile solvent may be removed by heat and/or vacuum. Either method produces a heated solution of the drug in the carrier. This heated solution is then chilled rapidly to form a solid solution which is then reduced in particle size, for use in the preparation of tablets or capsules.

The carriers which may be utilized in the present invention are polyethylene glycol polymers, pentaerythritol, pentaerythrityl tetraacetate or citric acid (e.g., monohydrous citric acid).

The preferred carrier utilized in the present invention is a polyethylene glycol polyer (PEG) which is solid at room temperature. Such solid polymers have a molecular weight of from 1,000 to 20,000 or higher and the polymers having an average molecular weight of from about 4,000 to 6,000 are preferred for purposes of the present invention. Suitable polymers are available commercially under the trademark CARBOWAX, Union Carbide Corporation.

This invention is applicable to any drug insoluble or relatively insoluble in body fluids which is soluble in the carrier or co-solvent utilized.

The invention is particularly useful in increasing the absorbability of drugs such as griseofulvin (gris), levo dopa, d-propoxyphene, meperidine, methadone, erthromycin, ampicillin, prednisone, prednisolone, benzodiazepines (e.g., temazepam, chordiazepoxide, and the like), codeine, methaqualone, steroidal estrogens, noscopien, digoxin, digitoxin, testosterone, methyl testosterone, oral contraceptives, hexobarbital, organic nitrates, such as pentaerythritol tetranitrate, and the like. Due to the nature of the organic nitrates, the solvent method but without the use of heat, is preferred for the preparation of these drug-carrier compositions.

In preparing the formulations of the present invention, a drug (e.g., griseofulvin) is first incorporated in the carrier (e.g., PEG) as a solution at a temperature of about 100° C. In the case of many drugs, this temperature can be exceeded in order to place the drug in solution and no mutual solvent is necessary. Thus if the drug is heat stable, the drug and the carrier are combined in the desired concentrations and heated to the temperature necessary to bring them into solution. If desired, a mutual solvent can be used such as N,N-dimethylformamide, N,N-dimethylacetamide, dimethylsulfoxide, butanol, ethanol, chloroform, and the like. The solvent is necessary if the drug will not otherwise go into solution at a temperature below its decomposition point. After the drug is in solution, the mixture is cooled to about 100° C. or other appropriate temperature depending on the nature of the drug and its concentration and the solvent is removed, using reduced pressure if necessary, to produce a melted solution of the drug in liquid carrier. It is not always necessary to remove the solvent completely but this should, of course, be done if the solvent is toxic. At this time the homogenous liquid may be shock cooled by passing it over a chilled roller or a metallic heat exchange system so that the mass is cooled in about a period of a few minutes to about room temperature (e.g., 10° C. to 30° C.). The plastic mass resulting from the cooling is now allowd to sit at about room temperature until the mass hardens. The time required for hardening, ranging from a few minutes to a few days, will depend on the nature of the drug and its concentration and the carrier used. For example, a preparation containing 2% of griseofulvin in PEG 6,000 requires less than one hour to harden. The mass can now be made up into tablets or capsules using conventional techniques.

Alternatively, the homogeneous liquid described above may be shock cooled by atomization into an inert liquid in which the drug and PEG are non-soluble, and which is maintained at a low temperature, e.g., −60° C. to 30° C. The homogeneous liquid is thus instantly cooled and particulated, and may be removed from the inert liquid, by conventional methods, such as filtration. For example, the homogeneous liquid may be injected into dry ice cooled heptane bath by means of an atomizer, e.g., needle, immersed in the heptane. The homogeneous liquid is instantly cooled and particulated in the heptane.

The particle size of PEG-drug composition prepared by this method may be controlled by the fineness of the atomization, and compositions thus prepared may be suitable for direct formulation into tablets or capsules using conventional techniques.

From 2 to 50% by weight of the desired drug can be incorporated in the carrier utilizing the above techniques. Naturally, the solvent will be employed in the case of those drugs which are heat labile while either simple melting or solvent can be used with heat stable drugs.

The following non-limiting Examples I to IX illustrate methods of making the preparations of the present invention. Examples X and XI are a dissolution rate study of drug-carrier compositions of this invention.

EXAMPLE I

A 10 gram mixture of 10% by weight of gris and 90% by weight of PEG 4,000 (number refer to average molecular weight of polyethylene glycol polymer) was prepared. The mixture was heated with a constant stirring on a hot plate until it was melted. This required a time of about 5 minutes and the maximum temperature was 180° C. The melt was then poured onto a stainless steel plate which was cooled by a stream of cold air or water (preferred temperature 0 to 25° C.) flowing on the opposite side of the plate. The mixture was thus cooled in a matter of a few minutes to substantially room temperature but at this point the mass was soft and not easily subdivided. The mixture was stored in a desicator at room temperature and after 48 hours, it was brittle and could be easily pulverized. The solid mass was then pulverized in a mortar or a ball mill and the powder was sieved to 80 to 200 mesh range. The powder could then be incorporated in tablets or capsules.

EXAMPLE II

The procedure similar to Example I was carried out (the maximum temperature used was higher for the higher concentration of the gris). PEG 6,000 was empolyed and the concentration of gris was 25%.

EXAMPLE III

The similar procedure of Example I was again carried out but this time PEG 20,000 was employed and the concentration of gris was 50%.

EXAMPLE IV

A mixture of 0.5 grams gris and 4.5 grams of PEG 6,000 was suspended in 500 ml. of absolute alcohol in a beaker and concentrated directly on a hot plate to about 100 ml. The resulting cloudy suspension was further concentrated on an oil bath, kept at 115° C. for one hour when the formation of ethanol vapor bubbles was no longer observed. The hot mixture was spread on a cool metal surface and cooled to room temperature rapidly. The sample was powdered and the 80 to 200 mesh fraction was collected.

EXAMPLE V

The similar procedure of Example IV was repeated except that a 20% gris mixture was prepared utilizing 1 gram of gris and 4 grams of PEG 6,000.

EXAMPLE VI

A mixture was made containing 5% hydrocortisone acetate and 95% PEG 6,000. The mixture was heated on a hot plate until dissolution was achieved and the material was then cooled rapidly as was described in Example I.

EXAMPLE VII

A mixture was prepared containing 5% of prednisolone acetate and 95% by weight PEG 6,000. This was processed in accordance with the procedure of Example I.

EXAMPLE VIII

A mixture was made containing 5% 17-methyltestosterene and 95% by weight of PEG 6,000. This was processed into a powder in accordance with the technique of Example I.

EXAMPLE IX

A mixture was made containing 2% digitoxin and 95% PEG 6,000. This was processed into a powder in accordance with the technique of Example I.

EXAMPLE X

Drug dissolution rate-studies were conducted to demonstrate the increase in the absorption rate of drugs following the teachings of this invention. The compositions of Table I were prepared as described in Example I. The studies were conducted as follows:

A recycling and automatic recording system was used for all dissolution rate studies. The dissolution rate of gris in different physical forms were run in 500 ml. distilled water in a 600 ml. beaker at room temperature.

Unless otherwise specified, samples of 80 to 200 mesh powder were transferred directly into the dissolution medium and stirred with a stainless steel paddle. The paddle, 5.5 × 2.7 cm., was placed at the center of a 500 ml. dissolution medium and rotated at a rate of 100 r.p.m. The solution was pumped by a peristatic pump (Multi-speed Transmission, model No. 6000-000, available from the Harvard Apparatus Co., Dover, Mass.) at a rate of 80 to 100 ml./min. through a glass filter stick to a 1-cm. flow cell and then back to the dissolution apparatus. The absorbance of the solution is monitored by a recording Beckman DB spectrophotometer at either the miximum peak of gris, 292 mu., or minimum absorbance, 272 mu. depending upon the concentration of gris. In the system of gris-PEG 20,000, 324 mu. was used because of possible interference of absorption by the polymer at 272 mu. The volume of the solution in the tubing of the recycling system is about 10 ml. At the flow rate used, the monitored absorbance will reach 90% of the equilibrium valve in 15 sec. Therefore, the lag time in the measurement of dissolution rate is essentially negligible. In the study of the dissolution rate at room temperature, the water is preadjusted to 25° C. The ambient temperature of the room ranged less than 2° from this temperature.

The solubility of gris at 25° C. is 1 mg/100 ml. of water, the amount of gris in the various solid dispersion systems used for the dissolution rate study in 500 ml. water was usually 5 mg., which would saturate this volume of the solvent.

Samples of micronized gris and of gris of 100 to 200 mesh particle size distribution were also run. They were prepared by rapidly melting and cooling gris and then pulverizing and sieving to 100 to 200 mesh or micronizing. All samples were run in duplicate.

The results are shown in Table I.

Table I

Twenty, Fifty, and Seventy Percent Dissolution Times for Various Griseofulvin Compositions in Saturation Dissolultion Apparatus[a]

| gris compositions | 20% min. | 50% min. | 70% min. |
|---|---|---|---|
| 100-200 Mesh pure gris | 60.0 | — | — |
| Micronizied gris (nonwetted) | 25.0 | — | — |
| Micronized gris (wetted) | 2.0 | 30.0-0.0 | — |
| 5% gris-PEG 6000 | 1.0 | 0.3 | 1.5 |
| 10% gris-PEG 6000 | 1.0 | 0.5 | 3.0 |
| 20% gris-PEG 6000 | 1.0 | 3.0 | 15.0 |
| 40% gris-PEG 6000 | 1.0 | 14.0 | — |
| 5% gris-PEG 4000 | 1.0 | 0.3 | 2.0 |
| 5% gris-PEG 20,000 | 1.0 | 0.6 | 2.5 |
| 20% gris-PEG 20,000 | 1.0 | 4.0 | — |
| 7.5% gris-pentaerythritol | 1.0 | 0.5 | 4.0 |
| 20% gris-pentaerythritol | 1.0 | 3.8 | 15.0 |
| 10% gris-Pentaerythrityl tetraacetate | 1.0 | 8.0 | — |
| 10% gris-succinic acid | 1.2 | 10.0 | 50.0 |
| 5% gris-citric acid | 1.0 | 0.2[b] | 0.3[b] |
| 20% gris-citric acid | 1.0 | 1.0 | 5.0 |

[a]Five milligrams gris in 500 ml. of water at 25°.
[b]Dissolution times taken from recorded absorbance readings. Values are not corrected for the circulation lag time of approximately 15 seconds.

Table I compares the studies utilizing the time it took for each preparation to reach 20% dissolution, 50% dissolution and 70% dissolution.

The dissolution rate of the nonwetted, micronized gris is markedly slower than that of the same powder when wetted first prior to study (with 2 ml. of 0.2% polysorbate (Tween 20) solution). Furthermore, the unwetted sample has almost the same dissolution rate as the 100-200 mish gris, thus indicating the serious agglomeration problem inherent with water-insoluble drugs, such as gris.

The strikingly fast dissolution rates of gris dispersed in various carrier systems are shown by this study. Even the preparation containing 40% of gris in the system of gris-PEG 6,000 (designated by 40% gris-PEG 6,000) possesses faster dissolution rate than the wetted micronized gris. This rapid dissolution may be attributed by the molecular and/or colloidal dispersion of gris in the carrier matrix. Owing to the similar physical and chemical properties of PEG 4,000, 6,000, and 20,000, it is understandable that gris dispersed in these three carriers all exhibit approximately the same dissolution characteristics.

A number of tests were made to establish that the gris was not decomposed in any manner following either the solvent or the direct fusion methods of preparing the solid solutions. The melting point, the spectra of the ultra-violet, the infrared and fluorescence are all identical to those of the gris used as a starting material. Thin layer chromatography was employed and no additional spots were detected on the material which had been formed into the solid solution.

Dissolution studies were similarly made involving other materials. In the case of pure prednisolone acetate it was found to require 8 minutes to achieve a 20% dissolution in water while a preparation made in accordance with Example VII required considerably less than 1 minute. In the case of pure methyltestosterone, the time for 20% dissolutiom was 2 minutes while the PEG solid solution required less than 1 minute. In the case of hydrocortisone acetate, more than 20 minutes were required for the pure material and considerably less than 1 minute for the solid solution with PEG 6,000.

In the case of the microcrystalline digitoxin, about 15 minutes were required while the solid solution with PEG 6,000 required less than 1 minute.

A series of experiments were made employing dogs, wherein oral preparations were fed to the dogs and blood samples withdrawn at intervals after feeding and the plasma analyzed for known metabolites of gris. In this series of experiments, it was found that the concentration of gris rose much more rapidly in the case of the solid solution of the present invention when compared with commercial micronized tablet and capsule preparations.

In order to establish that it was the physical form of the gris and not the mere presence of the PEG which contributed to the rapid rise, a comparison was made between 5% gris prepared as a solid solution in PEG 4,000 in accordance with the technique of the present invention and a similar preparation wherein 5% micronized gris was merely suspended in PEG 4,000. The results of these tests are shown in FIG. 1. It will be seen from FIG. 1 that the plasma concentration at about 100 minutes was only about 0.1 mcg. per ml. in the case of the gris which was merely suspended in PEG 4,000, while it averaged about 10 times this amount when fed as a solid solution prepared in accordance with the technique of the present invention.

In addition to drug, other materials which may or may not be biologically active may be incorporated in the PEG-drug system within the scope of this invention.

EXAMPLE XI

Bioavailability of Griseofulvin from GRIS-PEG

Using the GRIS-PEG formulations of this invention, the following two tests were run to determine the bioavailability (absorption) of griseofulvin.

Test #1

Thirty-six male volunteers were randomly assigned to three groups of equal size by means of a table of random numbers.

Group A (12 subjects) received a single, oral dose of 500 mg. of a commercially available formulation (tablet) of micronized griseofulvin. Group B (12 subjects) received two 125 mg. GRIS-PEG tablets (griseofulvin in a PEG-6,000 formulation, prepared as described in Example I). Group C (12 subjects) received four of the 125 mg. GRIS-PEG tablets. All subjects received the tablets at 8:00 a.m. with 4-6 ounces of water. Blood samples for the determination of the concentration of griseofulvin in plasma were obtained at zero time and at 0.5, 1, 2, 4, 6, 8, 10, 12, and 24 hours after the oral administration of the test medications.

Test #2

Twelve normal, healthy males participated in a doublebline, single dose crossover test. Group I received a single, oral dose of 500 mg. of a commercially available micronized formulation (tablet) with 4-6 ounces of water on Test Day 1. Group II received a single, oral dose of 250 mg. of the GRIS-PEG tablets of this invention with 4-6 ounces of water on Test Day 1. Assignment of subjects to a treatment group was based on a table of random numbers.

On Test Day 9, following a washout period, which extended from Test Day 3 to Test Day 8, the subjects were crossed over and received the second test medication.

Blood samples for the determination of the concentration of griseofulvin in the plasma were obtained at zero time and at 0.5, 1, 2, 4, 6, 8, 10, 12, 24, 36, 48, and 72 hours after the oral administration of the test medications.

The following variables were controlled in both Test #1 and Test #2.

All subjects were between the ages of 21 and 50 years, weighed between 140 and 200 pounds and were within ± 15% of the normal body weight for their frame and stature. Additional criteria for entrance into the tests included a normal routine physical examination, complete blood count, urinalysis and automated serum chemistries.

All subjects were totally free of significant clinical illness in the two weeks preceding the tests, had no surgical or medical condition which might interfere with the absorption, metabolism, or excretion of the study medications were not taking any other medication.

During the pretreatment phase (control period), the following parameters were studied in each subject; A 12-lead ECG, a battery of hematology tests, including a determination of the hemoglobin, hematocrit, and WBC count. Blood chemistries included a determination of the following: calcium, inorganic phosphorus, fasting blood sugar, BUN, serum uric acid, total protein, albumin, cholesterol, total bilirubin, alkaline phosphatase, LDH, and SGOT.

Subjects with abnormal values or findings were not admitted into the tests. These parameters were evaluated again on Test Day 2 in Test #1. They were also evaluated again in Test #2 on Test Day 2, at the end of the washout period, which was Test Day 8 and on Test Day 10.

No concurrent medication was permitted during the course of either Test #1 or #2.

Each subject fasted overnight but was allowed water ad lib. No food or liquids were allowed until four hours after the ingestion of the test medications.

A gas chromatographic method was employed to determine the concentration of griseofulvin in the plasma samples. The gas chromatographic method was an adaptation of the method reported by Shah, Riegelman, and Epstein [1] for the analysis of griseofulvin in skin samples.

[1]Shah, V.P.; Riegelman, S.; Epstein, W.L.: Determination of Griseofulvin in Skin, Plasma and Sweat, J. Pharm. Sci. 61: 634–636, 1972.

The following quantitative method was employed to determine the concentration of griseofulvin in plasma: A 2.0 ml sample of plasma was pipetted into a stoppered test tube; 2.0 ml of a saturated sodium chloride solution was added, followed by the addition of 10 ml of anhydrous ethyl ether. The tube was shaken for one minute. A 5 ml aliquot was then transferred to a pearshaped flask and the ether distilled off in vacuo. The residue was dissolved in 1.0 ml of glass distilled benzene containing 1.0 µg/ml of diazepam. A 5 µl aliquot of this solution was injected into the gas chromatograph.

The conditions of analysis were as follows:

| Column: | 3% OV 17 on Chromosorb W - 5 ft. |
| --- | --- |
| Temperatures: | Column - 027° C. |
| | Injection Port - 310° C. |
| | Electron Capture - 330° C. |
| Carrier Gas: | 10% methane - 90% argon |
| Flow: | 150 ml/min |
| Range: | 10 |
| Attenuation: | 16X |

Standard solutions of griseofulvin were made in benzene in the range of 0.1 to 2.0 µg/ml. Each standard solution also contained 1.00 µg/ml of diazepam as an internal standard. Five µl of each standard solution was injected under the same analysis condition as described above. Diazepam was found to have a retention time of ~3 minutes while griseofulvin appeared in ~8 minutes.

The peak heights ratio diazepam:griseofulvin was plotted against the concentration of griseofulvin. The curve was linear between concentrations of 0.1 to 1.5 µg/ml. The sensitivity of the method was 0.1 µg/ml. The response below 0.1 µg/ml was found to be too small compared to the internal standard. Recovery of griseofulvin added to human plasma varied from 96–118% with an average value of 103%. The standard deviations were approximately 10% for all concentrations employed. The gas chromatographic method especially with the electron capture detector was considered to be specific for griseofulvin.

RESULTS

Test #1—Parallel Group Design

Figure 2:
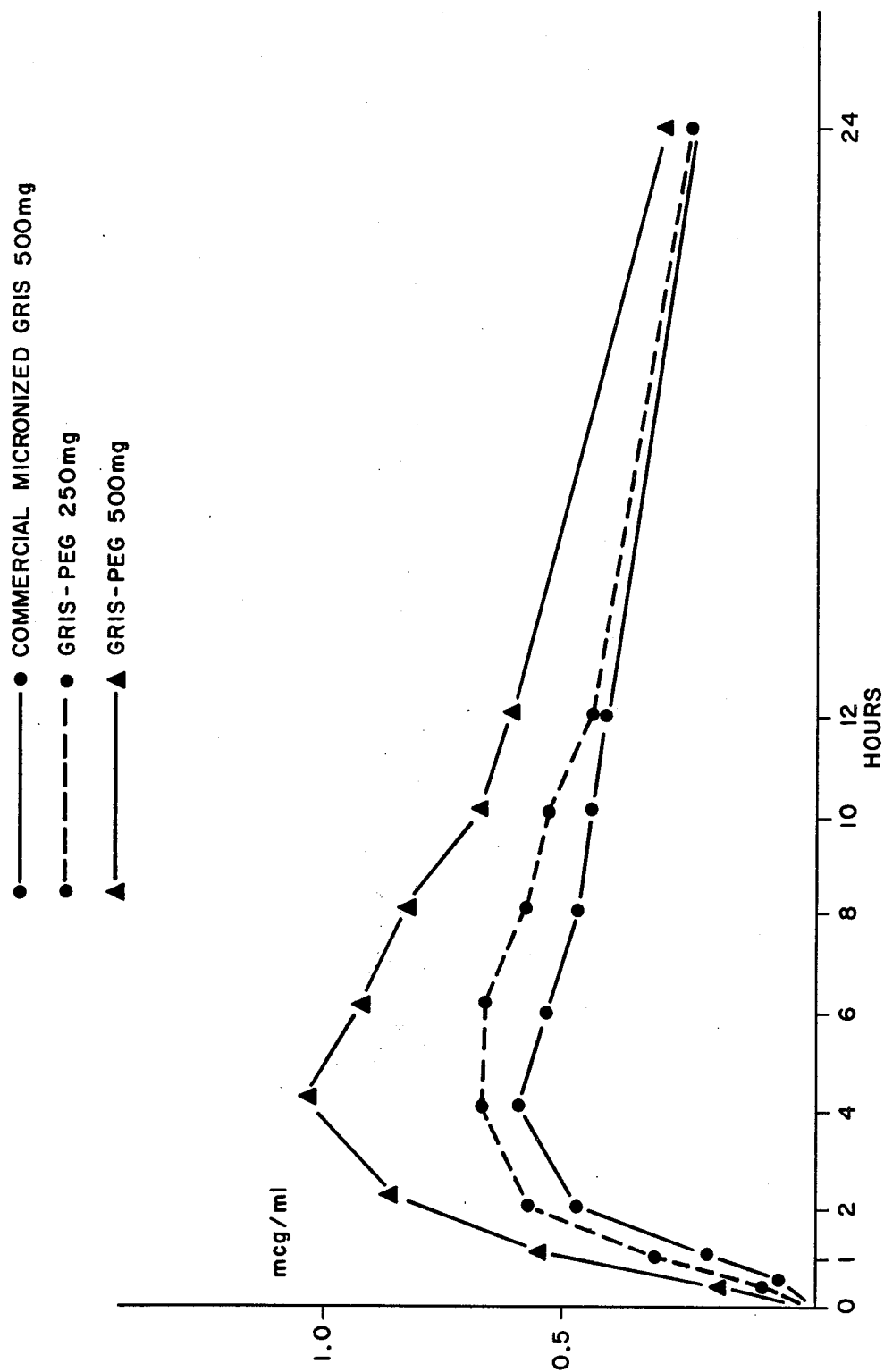

A single, oral dose of 250 mg. of GRIS-PEG produced essentially the same peak plasma concentration, the same time to reach peak concentration, and the same area under the plasma level curve as was achieved with a single, oral dose of 500 mg. of the micronized formulation of griseofulvin (see FIG. 2).

Following the oral administration of a single 500 mg. dose of GRIS-PEG, the peak plasma level and the area under the plasma level curve were significantly enhanced when compared to the results achieved with a 500 mg. dose of a commercially available micronized formulation of griseofulvin (see FIG. 2).

Test #1A—Crossover Design

Figure 3:
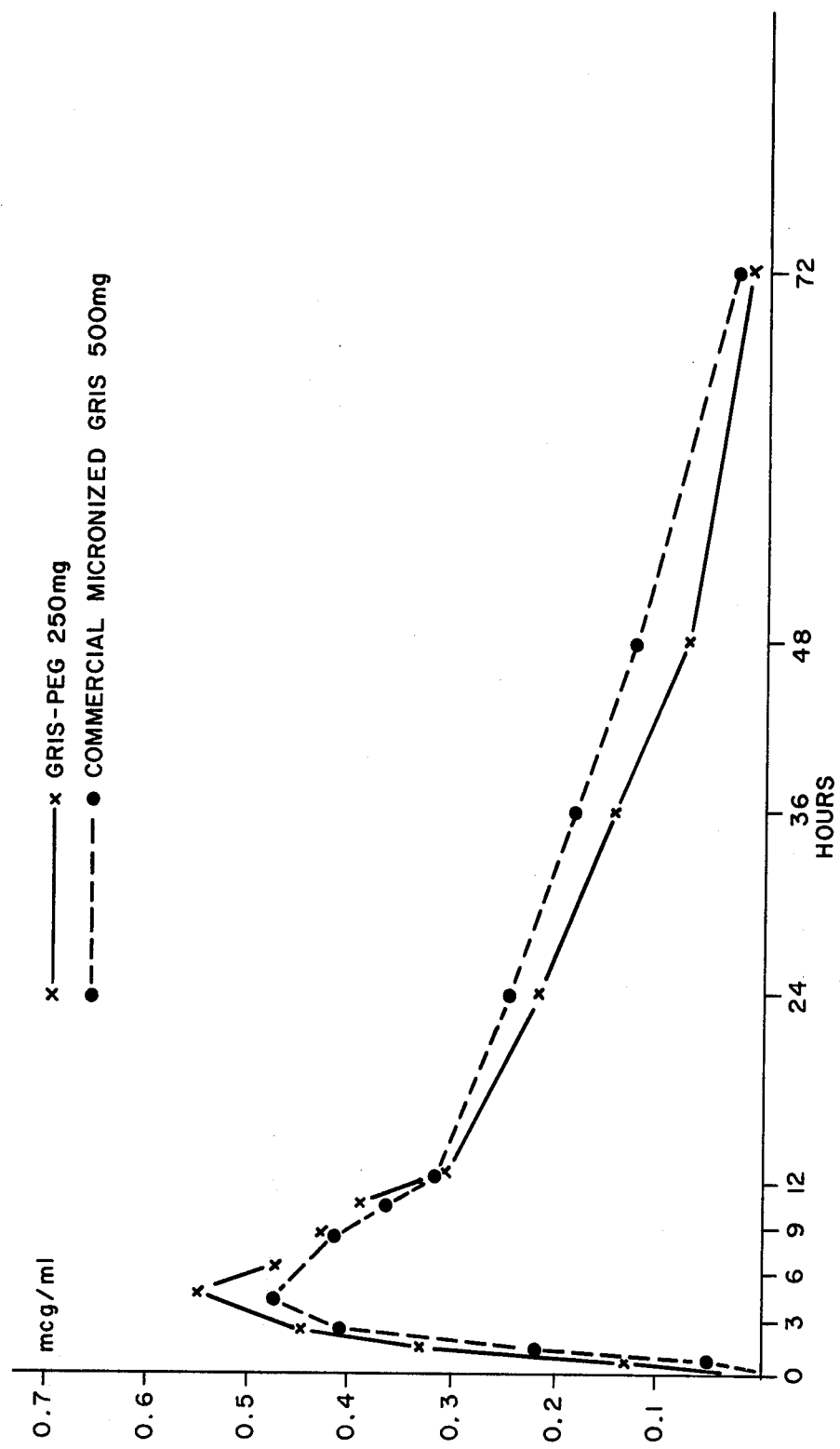

In this crossover study, an oral dose of 250 mg. of GRIS-PEG produced essentially the same peak concentration and the same area under the plasma level as was achieved with a single, oral dose of 500 mg. of a commercially available micronized formulation of griseofulvin (see FIG. 3).

In Tests #1 and #2, no adverse effects attributable to the study medications were observed in the following parameters: vital signs, ECG, hematology parameters, blood chemistry parameters, and the urinalysis tests. No adverse reactions were reported during the course of these two tests.

The results of the above two tests show that the oral absorption of griseofulvin is unexpectedly and unobviously enhanced by the GRIS-PEG formulation of this invention and that the same plasma levels were achieved with 250 mg. of GRIS-PEG as were achieved with a 500 mg. oral dose of a commercial micronized formulation of griseofulvin.

What is claimed is:

1. In the art of obtaining an effective concentration of griseofulvin of a single, oral dosage in humans, the improvement of administering to a human subject an effective concentration dosage of griseofulvin which has been prepared by forming a mixture of polyethylene glycol having an average molecular weight of from 1,000 to 20,000 and from about 2% to about 50% of griseofulvin, heating the mixture to an elevated temperature sufficient to dissolve the griseofulvin without decomposition in the polyethylene glycol and rapidly cooling instantaneously within 2 to 3 minutes, the griseofulvin-polyethylene glycol mixture to produce a solid solution of griseofulvin in the polyethylene glycol.

2. The method according to claim 1, wherein the solid solution is ground to a fine powder.

3. In a process for making a solid solution of polyethylene glycol and griseofulvin comprising heating to an elevated temperature without decomposition of the griseofulvin a mixture of polyethylene glycol having an average molecular weight of from 1,000 to 20,000 and from about 2% to about 50% of griseofulvin, the step of rapidly cooling instantaneously within 2 to 3 minutes the polyethylene glycolgriseofulvin mixture to produce a solid solution of the griseofulvin in the polyethylene glycol.

4. The product prepared by the process of claim 3.

5. A process for making a solid solution of polyethylene glycol and griseofulvin comprising forming a mixture of polyethylene glycol having an average molecular weight of from 1,000 to 20,000 and from about 2% to about 50% of griseofulvin, heating the mixture to an elevated temperature sufficient to dissolve the griseofulvin without decomposition in the polyethylene glycol, and rapidly cooling instantaneously within 2 to 3 minutes the polyethylene glycol-griseofulvin mixture to produce a solid solution of the griseofulvin in the polyethylene glycol.

6. The product prepared by the process of claim 5.

7. A process for making a solid solution of polyethylene glycol and griseofulvin comprising adding a mixture of polyethylene glycol having an average molecular weight of from 1,000 to 20,000 and from about 2% to about 50% of griseofulvin to a mutual solvent, heating the polyethylene glycol-griseofulvin-solvent mixture to form a solution, removing substantially all of the solvent, and rapidly cooling instantaneously within 2 to 3 minutes, the resultant polyethylene glycol-griseofulvin mixture to produce a solid solution of the griseofulvin in the polyethylene glycol.

8. The product prepared by the process of claim 7.

9. In the art of obtaining an effective concentration of griseofulvin of a single, oral dosage in humans, the improvement of administering to a human subject an effective concentration dosage of griseofulvin which has been prepared by adding a mixture of polyethylene glycol having an average molecular weight of from 1,000 to 20,000 and from about 2% to about 50% of griseofulvin to a mutual solvent, heating the polyethylene glycol-griseofulvin-solvent mixture to form a solution, removing substantially all of the solvent, and rapidly cooling instantaneously within 2 to 3 minutes, the griseofulvin-polyethylene glycol mixture to produce a solid solution of griseofulvin in polyethylene glycol.

10. The method according to claim 9, wherein the solid solution is ground to a fine powder.

11. In the art of obtaining an effective concentration of griseofulvin of a single, oral dosage in humans, the improvement of administering to a human subject an effective concentration dosage of griseofulvin which has been prepared by heating to an elevated temperature without decomposition of the griseofulvin, a mixture of polyethylene glycol having an average molecular weight of from 1,000 to 20,000 and from about 2% to about 50% of griseofulvin, and rapidly cooling instantaneously within 2 to 3 minutes, the griseofulvin-polyethylene glycol mixture to produce a solid solution of griseofulvin in polyethylene glycol.

12. The method according to claim 11, wherein the solid solution is ground to a fine powder.

* * * * *